United States Patent
Ataka et al.

(10) Patent No.: US 7,332,632 B2
(45) Date of Patent: Feb. 19, 2008

(54) METHOD FOR PRODUCING ALDEHYDE COMPOUND OR KETONE COMPOUND BY USING MICROREACTOR

(75) Inventors: Kikuo Ataka, Ube (JP); Hiroyuki Miyata, Ube (JP); Tatsuya Kawaguchi, Ube (JP); Junichi Yoshida, Hirakata (JP); Kazuhiro Mae, Kyoto (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 10/587,369

(22) PCT Filed: Nov. 22, 2004

(86) PCT No.: PCT/JP2004/017666

§ 371 (c)(1),
(2), (4) Date: Jul. 26, 2006

(87) PCT Pub. No.: WO2005/073155

PCT Pub. Date: Nov. 8, 2005

(65) Prior Publication Data

US 2007/0149823 A1    Jun. 28, 2007

(30) Foreign Application Priority Data

Jan. 28, 2004  (JP) .................... 2004-020166

(51) Int. Cl.
*C07C 45/00* (2006.01)
(52) U.S. Cl. .............. 568/322; 568/361; 568/363; 568/403; 568/485
(58) Field of Classification Search .............. None
See application file for complete search history.

(56) References Cited

U.S. PATENT DOCUMENTS 4,585,622 A * 4/1986 Bowe et al. ............. 422/50
6,960,235 B2 * 11/2005 Morse et al. ............. 48/127.9
6,974,693 B2 * 12/2005 Barlocchi et al. ........ 435/288.5
2002/0055655 A1 * 5/2002 Leipprand et al. .......... 568/313

FOREIGN PATENT DOCUMENTS

| JP | 57-175138 A | 10/1982 |
| JP | 2002-155007 A | 5/2002 |
| JP | 2003-506339 A | 2/2003 |
| JP | 2003-113185 A | 4/2003 |
| JP | 2003-128677 A | 5/2003 |
| WO | 03/064363 A1 | 8/2003 |

OTHER PUBLICATIONS

Omura, Kanji et al., "Dimethyl Sulfoxide-Trifluoroacetic Anhydride: a New Reagent for Oxidation of Alcohols to Carbonyls", J. Org. Chem., 1976, vol. 41, No. 6, pp. 957 to 962.
Appendino, Giovanni et al., "Reaction of 4-Hydroxycoumarin Derivatives with Activated Dimethyl Sulphoxide", J. Chem. Soc., Perkin Trans. 1, 1989, pp. 2305 to 2309.
Yu Ming Lin et al., "Activity and stability of a copper (II) oxide-zinc (II) oxide catalyst for oxidative dehydrogenation of cyclohexanol to Cyclohexanone", Abstract, *Applied Catalysts*, 1988, vol, 41, pp. 53-63.

* cited by examiner

*Primary Examiner*—Sikarl A. Witherspoon
(74) *Attorney, Agent, or Firm*—DLA Piper US LLP

(57) ABSTRACT

The method for producing an aldehyde or ketone compound from a corresponding primary or secondary alcohol at relatively high temperature within a short time with a high yield including a step (1) of reacting a sulfoxide compound with an activating agent to produce an activation reaction product; a step (2) of reacting the activation reaction product with a primary or secondary alcohol to produce an alkoxysulfonium salt; and a step (3) of reacting the reaction product with a base to produce an aldehyde or ketone; wherein at least one of the steps, preferably the step (1) and step (2), are carried out by using a microreactor.

23 Claims, No Drawings

US 7,332,632 B2

METHOD FOR PRODUCING ALDEHYDE COMPOUND OR KETONE COMPOUND BY USING MICROREACTOR

RELATED APPLICATION

This is a 371 of International Application No. PCT/JP2004/017666, with an international filing date of Nov. 22, 2004 (WO 2005/073155 A1, published Aug. 11, 2005), which is based on Japanese Patent Application No. 2004-020166, filed Jan. 28, 2004.

TECHNICAL FIELD

This disclosure relates to a method for producing an aldehyde compound or a ketone compound using a microreactor, particularly to a method for producing an aldehyde or ketone compound from a primary or secondary alcohol and through the Swern oxidation reaction using a microreactor.

BACKGROUND

When the Swern oxidation reaction is used to produce an aldehyde compound or a ketone compound from a primary or secondary alcohol, no waste containing a heavy metal is produced and the reaction can be widely applied to various compounds. Also no excess oxidation arises and epimerization, at the α-position with respect to a carbonyl group, does not arise. Therefore, this method is widely used as an organic synthesis reaction method.

However, the Swern oxidation reaction has a problem in that an activation reaction product of a sulfoxide compound and an intermediate of an alkoxysulfonium salt are thermally unstable and, also, by-products are likely to be produced by Pummerer rearrangement at a temperature of −30° C. or higher. To solve this problem, in a conventional method, the reaction temperature must be securely controlled to a low temperature such as −50° C. or lower. Such a low temperature reaction is expensive and requires a long reaction time and it is actually difficult to control the temperature. It is difficult to scale up this method from an industrial point of view.

As a trial using a microreactor for an organic chemical reaction, for example, Japanese Unexamined Patent Publication (Kokai) No. 2002-155007 discloses that a fine-structured reaction system is used so as to produce aldols from aldehydes and/or ketones at a temperature of −10 to +250° C. through a catalytic reaction, while Japanese Unexamined Patent Publication (Kokai) No. 2003-113185 discloses a method, for producing an allylboron compound and an alkylboron compound, which comprises reacting a lithium aromatic and an aliphatic compound with a boron compound at a temperature of −60° C. to +30° C. using a microreactor.

Furthermore, Kohyo (National Publication of Translated Version) No. 2003-506339 discloses a method for a Friedel-Crafts acylation reaction of an acylating agent and strong acid with an organic compound (preferably, an aromatic or heteroaromatic compound) in a microreactor at a temperature of 10 to 90° C. Furthermore, Japanese Unexamined Patent Publication (Kokai) No. 2003-128677 discloses a method, for producing an allylboron and an alkylboron, which comprises reacting a halide of allylmagnesium and alkylmagnesium with a boron compound in a microreactor at a temperature of −60° C. to +80° C.

However, there has never been known a method capable of industrially carrying out the Swern reaction of a primary or secondary alcohol using a microreactor.

SUMMARY

We provide methods for producing an aldehyde compound or a ketone compound from a primary or secondary alcohol at a higher temperature than that in case of a conventional method, within a short time and with a high yield.

The method for producing an aldehyde compound or a ketone compound using a microreactor, comprises a step (1) of mixing a liquid containing a sulfoxide compound with a liquid containing an activating agent for the sulfoxide compound to allow them to react with each other and to produce an activation reaction product of the sulfoxide compound; a step (2) of mixing the liquid containing the activation reaction product of the sulfoxide compound with a liquid containing at least one member selected from primary and secondary alcohols to allow them to react to each other and to prepare a liquid containing an alkoxysulfonium salt; and a step (3) of mixing the resulting liquid containing an alkoxysulfonium salt with a basic compound-containing liquid and to allow them to react with each other and to prepare a liquid containing an aldehyde compound or a ketone compound corresponding to the alkyl alcohol, wherein at least one step of the steps (1), (2) and (3) is carried out using a microreactor.

The microreactor preferably comprises two liquid-introducing channels having a fine cross-sectional profile for introducing two type of liquids; one micromixer portion, for mixing and reacting the two kinds of introduced liquids with each other, having a fine cross-sectional profile and connected to the liquid introducing channel; and one liquid discharging channel for discharging a reaction product liquid from the micromixer portion, having a fine cross-sectional profile.

Preferably, two steps connected to each other are carried out by using a microreactor and a liquid discharging channel of a rector of an upstream step and a liquid introducing channel of a reactor of a downstream step connected to the upstream step, are connected with each other through a connecting capillary tube.

The steps (1) and (2) are preferably carried out in the microreactor.

The temperatures of the liquids in the micromixer portion and the liquid discharging channel of the microreactor are preferably adjusted to a desired values.

The temperature of the liquids in the connecting capillary tube is preferably adjusted to a desired value.

Preferably, the cross-sectional area of the liquid introducing channel, that of the liquid micromixer portion and that of the liquid discharging channel in the microreactor, are respectively 0.7 μm$^2$ to 1 mm$^2$, 0.7 μm$^2$ to 1 mm$^2$ and 0.7 μm$^2$ to 1 mm$^2$.

A major diameter/minor diameter ratio of the cross section of the liquid introducing channel, the liquid micromixer portion and the liquid discharging channel in the microreactor, is preferably 1 or more and the minor diameter is preferably within a range from 1 μm to 1 mm.

Preferably, in the microreactor, the flow rate of the liquid to be discharged from the liquid micromixer is adjusted so that two kinds of liquids mixed with each other can be reacted to each other in the microreactor with a desired mixing efficiency and a desired retention time.

The residence time of the liquid in the microreactor is preferably adjusted within a range from 0.001 to 60 seconds.

Preferably, step (1) is carried out using a microreactor and the residence time of a mixed reaction solution of the sulfoxide compound-containing liquid with an activating agent-containing liquid in a portion of the microreactor between the inlet of the micromixer portion and the inlet of the reactor for the step (2) is in the range of from 0.001 to 60 seconds.

Preferably, step (1) is carried out in the microreactor and the reaction temperature in step (1) is in the range of from −80 to +50° C., more preferably from −30 to +40° C.

Preferably, the step (2) is carried out in the microreactor and the mixing reaction temperature in the step (2) is in the range of from −80 to +50° C., more preferably from −30 to +40° C.

The sulfoxide compound is preferably selected from a dialkyl sulfoxide.

Dimethyl sulfoxide is preferably used as a dialkyl sulfoxide.

The activating agent for a sulfoxide compound is preferably selected from acetic anhydride, oxalyl chloride, trifluoroacetic anhydride, trifluoromethanesulfonic anhydride, diphosphorus pentaoxide, chlorine, benzoyl chloride, acetyl chloride, methanesulfonyl chloride, p-toluenesulfonyl chloride, sulfur trioxide-pyridine complex and 2,4,6-trichloro-1,3,5-triazine.

The primary and secondary alcohols are preferably selected from saturated and unsaturated $C_1$-$C_{20}$ aliphatic primary and secondary alcohols, or saturated and unsaturated aliphatic primary and secondary alcohols having an alicyclic aromatic hydrocarbon group, and saturated and unsaturated primary and secondary alcohols having a heterocyclic group.

The basic compound is preferably selected from organic amine compounds.

The organic amine compound is preferably selected from trialkylamines.

A molar ratio of the sulfoxide compound to be supplied to the first step to the primary or secondary alcohol to be supplied to the second step is preferably within a range of from 1:1 to 20:1.

A molar ratio of the activating agent for a sulfoxide compound to be supplied to the first step to the primary or secondary alcohol to be supplied to the second step is preferably within a range of from 1:1 to 2:1.

A molar amount of the base compound to be supplied to the third step is preferably 2 to 20 times the molar amount of the primary or secondary alcohol to be supplied to the second step.

The methods may further comprise a step of isolating the target aldehyde or ketone compound from the aldehyde or ketone compound-containing liquid prepared in the step (3).

When an aldehyde compound or a ketone compound is produced from a corresponding primary or secondary alcohol, the use of a microreactor in at least one step of the method enables a relatively high temperature of, for example, about 20° C. to use in place of a low temperature of −50° C. used in the conventional method, and the target compound to be produced at a high yield within a short time.

DETAILED DESCRIPTION

The method for producing a corresponding aldehyde compound or a corresponding ketone compound by using a microreactor comprises:

a step (1) of mixing a liquid containing a sulfoxide compound with a liquid containing an activating agent for the sulfoxide compound to allow them to react with each other and to produce an activation reaction product of the sulfoxide compound;

a step (2) of mixing the liquid containing the activation reaction product of the sulfoxide compound with a liquid containing at least one member selected from primary and secondary alcohols to allow them to react with each other and to prepare a liquid containing an alkoxysulfonium salt; and a step (3) of mixing the resulting liquid containing an alkoxysulfonium salt with a basic compound-containing liquid to allow them to react with each other and to prepare a liquid containing an aldehyde compound or a ketone compound corresponding to the alkyl alcohol, wherein at least one step of the steps (1), (2) and (3) is carried out by using a microreactor.

The microreactor is preferably used in at least two of steps (1), (2) and (3), more preferably in the steps (1) and (2), and still more preferably in the three steps (1), (2) and (3).

The steps (1), (2) and (3) are carried out according to the following reaction scheme (1):

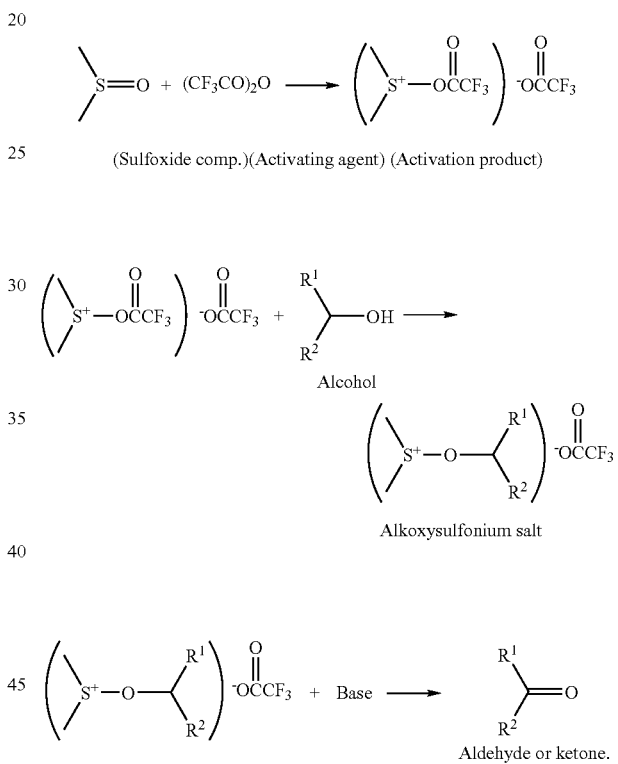

In the formulae, $R^1$ and $R^2$ respectively and independently from each other represent a hydrocarbon group or a heterocyclic organic group, $R^1$ and $R^2$ may be combined with each other to form a cyclic group, or one of $R^1$ and $R^2$ represents a hydrocarbon group or a heterocyclic organic group and the other one represents a hydrogen atom.

The structure of the microreactor usable for the method of the present invention is not specifically limited, but the microreactor preferably comprises two liquid-introducing channels for introducing two kinds of liquids having a fine cross-sectional profile; one micromixer portion, for mixing and reacting two kinds of liquids introduced, having a fine cross-sectional profile and connected to the liquid-introducing channel; and one liquid discharging channel for discharging the resultant reaction product liquid from the micromixer portion, having a fine cross-sectional profile.

In the micromixer portion as mentioned above, two kinds of liquids are uniformly mixed with each other and in the micromixer portion and the liquid discharging channel the temperature of the mixed liquid is adjusted to a desired temperature.

In the case where two steps connected to each other are carried out by using microreactors, a liquid-discharging channel of a reactor of the upstream step and a liquid-discharging channel of a reactor of the downstream step are preferably connected with each other through a connecting capillary tube. The temperature of the liquid mixture obtained by uniform mixing in the micromixer can be adjusted to a desired temperature in the micromixer and the liquid-discharging channel and also the desired reaction can be allowed to proceed and complete. The connecting capillary tube is preferably provided with means for adjusting the temperature of the liquid which flows through the connecting capillary tube. The means may be a constant temperature bath, a temperature control jacket or the like.

As described above, as described above, the microreactor is preferably used in at least the two steps (1) and (2). Thereby, main reaction steps (1) and (2) can be accurately controlled and the respective reactions can be completed within a reduced time and with high efficiency.

In the microreactor, the areas of the cross-sections of the liquid-introducing channel, the liquid micromixer portion and the liquid-discharging channel are respectively and preferably from 0.7 $\mu m^2$ to 1 $mm^2$ (more preferably from 0.007 to 0.7 $mm^2$), 0.7 $\mu m^2$ to 1 $mm^2$ (more preferably from 0.007 to 0.7 $mm^2$) and 0.7 $\mu m^2$ to 1 $mm^2$ (more preferably from 0.007 to 0.7 $mm^2$), and the major diameter/minor diameter ratios of the cross sections are preferably 1 or more and the minor diameters of the cross-sections are preferably within a range from 1 $\mu m$ to 1 mm, and more preferably from 25 to 500 $\mu m$.

In the microreactor, the flow rate of the liquid to be discharged from the liquid micromixer is defined so as to react two kinds of liquids mixed in the microreactor with a desired mixing efficiency and a desired residence time.

Each reaction time in the reactions (1), (2) and (3) can be appropriately adjusted, but the residence time of the liquid in the microreactor is preferably adjusted to within a range of from 0.001 to 60 seconds. The step (1) is preferably carried out in the microreactor and the mixing reaction temperature is preferably from −30 to +50° C., and also the step (2) is preferably carried out in the microreactor and the mixing reaction temperature is preferably from −80 to +50° C., and more preferably from −30 to +40° C.

In case of the step of using no microreactor, a reactor comprising two liquid supply means and one product liquid discharging means, for example, a T joint type reactor can be used. The reactor is preferably provided with temperature-adjusting means, liquid flow rate-adjusting means, etc.

The sulfoxide compound to be supplied to the step (1) is preferably selected from a dialkyl sulfoxide and, more preferably, dimethyl sulfoxide is used. As the liquid containing a sulfoxide compound, an organic solvent solution of the sulfoxide compound is usually used. If the sulfoxide compound is liquid, it can be used at it is.

The organic solvent us not specifically limited as far as it is a solvent which has hitherto been in the Swern oxidation reaction, and examples thereof include chlorinated hydrocarbons such as methylene chloride, 1,2-dichloroethane, chlorobenzene and 1,2-dichlorobenzene; aromatic hydrocarbons such as benzene, toluene and xylene; ethers such as diethyl ether, diisopropyl ether, dibutyl ether, dimethoxyethane, tetrahydrofuran and dioxane; saturated hydrocarbons such as pentane, hexane, heptane, octane and cyclohexane; and acetonitrile, propionitrile and hexamethylphophoramide (HMPA). Preferably, methylene chloride, toluene and chlorobenzene are used.

The concentration of the sulfoxide compound in the liquid containing a sulfoxide compound is preferably from 0.1 to 20 mol/liter.

The activating agent for a sulfoxide compound to be used in the step (1) of the method is preferably selected from acetic anhydride, oxalyl chloride, trifluoroacetic anhydride, trifluoromethanesulfonic anhydride, diphosphorus pentaoxide, chlorine, benzoyl chloride, acetyl chloride, methanesulfonyl chloride, p-toluenesulfonyl chloride, sulfur trioxide-pyridine complex and 2,4,6-trichloro-1,3,5-triazin and, more preferably, trifluoroacetic anhydride and oxalyl chloride are used. The activating agent-containing liquid can be prepared by dissolving an activating agent in an organic solvent. This organic solvent is preferably the same as the organic solvent for a sulfoxide compound. The concentration of the activating agent in the activating agent-containing liquid is preferably from 0.1 to 15 mol/liter.

In the step (1) of the method, as shown in the step (1) of the reaction scheme (1), a sulfoxide compound is reacted with an activating agent (for example, trifluoroacetic anhydride) to produce an activation reaction product of the sulfoxide compound. The activation reaction product produced in the step (1) is unstable and exhibits the following tendency. Namely, at the temperature of −30° C. or higher, Pummerer rearrangement occurs on the activation reaction product to cause the activation reaction product to be decomposed into $CH_3S^+=CH_2$ and $CF_3CO_2H$ and, furthermore decomposition products to produce $CH_3SCH_2OC(O)CF_3$, or in the step (2), the decomposition reaction product reacts with a primary or secondary alcohol to produce $R_1(R^2)$—$OCH_2SCH_3$ (MTM ether), and in the step (3), $CH_3SCH_2OC(O)CF_3$ reacts with a base to produce $R_1(R^2)$—$OC(O)CF_3$ (TFA ester). When the reaction in the step (1) is completed by vigorous mixing using a microreactor and accurately control at a predetermined temperature, it becomes possible to prevent or reduce the Pummerer rearrangement and to feed an activation reaction product-containing liquid into the step (2).

In step (2) of the method, the activation reaction product-containing liquid introduced from the step (1) and a liquid containing at least one of primary and secondary alcohols are mixed and reacted to prepare a liquid containing an alkoxysulfonium salt shown in the step (2) of the reaction scheme (1).

The primary and secondary alcohols to be used in the step (2) of the method are not noticeably limited as far as they are a primary alcohol and a secondary alcohol (which have an OH group combined with carbon atoms of an aliphatic hydrocarbon group but not with carbon atoms constituting an aromatic ring (namely not a phenolic OH group)). The primary and secondary alcohols include the followings:

(1) $C_1$-$C_{20}$ Saturated and unsaturated aliphatic primary alcohols, for example, methyl alcohol, ethyl alcohol, n-propyl alcohol, butyl alcohol, isobutyl alcohol, pentyl alcohol, isopentyl alcohol, neopentyl alcohol, hexyl alcohol, isohexyl alcohol, heptyl alcohol, octyl alcohol, 2-ethylhexyl alcohol, nonyl alcohol, decyl alcohol, allyl alcohol, crotyl alcohol, propargyl alcohol, geraniol and phytol;

(2) alicyclic primary alcohols in which an —OH group is combined with carbon atoms of a $C_1$-$C_{12}$ alicyclic hydrocarbon ring via a linear hydrocarbon group having one or more carbon atoms, for example, cyclohexylmethyl alcohol, 2-norbornane methanol and 5-norbornene-2-methanol;

(3) aromatic primary alcohols in which an —OH group is combined with carbon atoms of an aromatic hydrocarbon ring via an alicyclic hydrocarbon group having one or more carbon atoms, for example, benzyl alcohol, phenethyl alcohol, cinnamyl alcohol, salicyl alcohol and 2-phenyl ethanol;

(4) heterocyclic primary alcohols in which an —OH group is combined with carbon atoms of a heterocyclic group via a $C_1$ linear hydrocarbon group having one or more carbon atoms, for example, furfuryl alcohol;

(5) $C_3$-$C_{20}$ saturated and unsaturated aliphatic secondary alcohols, for example, 2-propanol, 2-butanol, 2-pentanol, 3-pentanol, 2-hexanol, 3-hexanol, 2-heptanol, 3-heptanol, 4-heptanol, 2-octanol, 3-octanol, 4-octanol, 2-nonanol, 3-nonanol, 4-nonanol and 5-nonanol;

(6) $C_3$-$C_{20}$ alicyclic secondary alcohols, for example, cyclopentanol, 2-methylcyclopentanol, 3-methylcyclopentanol, 2-ethylcyclopentanol, 3, ethylcyclopentanol, 2-n-propylcyclopentanol, 3-n-propylcyclopentanol, 2-isopropylcyclopentanol, 3-isopropylcyclopentanol, 2-n-butylcyclopentanol, 3-n-butylcyclopentanol, 2-isobutylcyclopentanol, 3-isobutylcyclopentanol, 2-sec-butylcyclopentanol, 3-sec-butylcyclopentanol, 2-tert-butylcyclopentanol, 3-tert-butylcyclopentanol; cyclohexanol, 2-methylcyclohexanol, 3-methylcyclohexanol, 4-methylcyclohexanol, 2-ethylcyclohexanol, 3-ethylcyclohexanol, 4-ethylcyclohexanol, 2-n-propylcyclohexanol, 3-n-propylcyclohexanol, 4-n-propylcyclohexanol, 2-isopropylcyclohexanol, 3-isopropylcyclohexanol, 4-isopropylcyclohexanol, 2-n-butylcyclohexanol, 3-n-butylcyclohexanol, 4-n-butylcyclohexanol, 2-isobutylcyclohexanol, 3-isobutylcyclohexanol, 4-isobutylcyclohexanol, 2-sec-butylcyclohexanol, 3-sec-butylcyclohexanol, 4-sec-butylcyclohexanol, 2-tert-butylcyclohexanol, 3-tert-butylcyclohexanol, 4-tert-butylcyclohexanol; cycloheptanol, 2-methylcycloheptanol, 3-methylcycloheptanol, 4-methylcycloheptanol, 2-ethylcycloheptanol, 3-ethylcycloheptanol, 4-ethylcycloheptanol, 2-n-propylcycloheptanol, 3-n-propylcycloheptanol, 4-n-propylcycloheptanol, 2-isopropylcycloheptanol, 3-isopropylcycloheptanol, 4-isopropylcycloheptanol, 2-n-butylcycloheptanol, 3-n-butylcycloheptanol, 4-n-butylcycloheptanol, 2-isobutylcycloheptanol, 3-isobutylcycloheptanol, 4-isobutylcycloheptanol, 2-sec-butylcycloheptanol, 3-sec-butylcycloheptanol, 4-sec-butylcycloheptanol, 2-tert-butylcycloheptanol, 3-tert-butylcycloheptanol, 4-tert-butylcycloheptanol; cyclooctanol, 2-methylcyclooctanol, 3-methylcyclooctanol, 4-methylcyclooctanol, 5-methylcyclooctanol, 2-ethylcyclooctanol, 3-ethylcyclooctanol, 4-ethylcyclooctanol, 5-ethylcyclooctanol, 2-n-propylcyclooctanol, 3-n-propylcyclooctanol, 4-n-propylcyclooctanol, 5-n-propylcyclooctanol, 2-isopropylcyclooctanol, 3-isopropylcyclooctanol, 4-isopropylcyclooctanol, 5-isopropylcyclooctanol, 2-n-butylcyclooctanol, 3-n-butylcyclooctanol, 4-n-butylcyclooctanol, 5-n-butylcyclooctanol, 2-isobutylcyclooctanol, 3-isobutylcyclooctanol, 4-isobutylcyclooctanol, 5-isobutylcyclooctanol, 2-sec-butylcyclooctanol, 3-sec-butylcyclooctanol, 4-sec-butylcyclooctanol, 5-sec-butylcyclooctanol, 2-tert-butylcyclooctanol, 3-tert-butylcyclooctanol, 4-tert-butylcyclooctanol, 5-tert-butylcyclooctanol; decahydro-1-naphthol, decahydro-2-naphthol, norborneol and isoborneol.

In the step (2) of the method, when a solid is formed by the reaction of the primary alcohol or secondary alcohol at the reaction temperature in the step (2), the solid is used after dissolving it in the same organic solvent as the organic solvent for the step (1). The concentration of the alcohol is preferably from 0.1 to 15 mol/liter.

When the step (2) of the method is carried out in the microreactor, a rearrangement reaction of the alkoxysulfonium salt shown in the formula (1) is prevented or reduced and the resulting alkoxysulfonium salt-containing liquid can be fed into the step (3).

In the step (3) of the method, the alkoxysulfonium salt-containing liquid is mixed with a basic compound-containing liquid and they are reacted with each other to prepare a liquid containing an aldehyde or ketone compound corresponding to the primary or secondary alcohol.

The basic compound is preferably selected from an organic amine compound, for example, alkylamine compound, triethylamine, tripropylamine, tributylamine, diethylmethylamine, diethylcyclohexylamine and diisopropylamine, more preferably selected from a trialkylamine and, still more preferably, trimethylamine is used. When the basic compound to be used cannot be in a liquid form at the reaction temperature of the step (3), it can be used after dissolving in the same solvent as the organic solvent used in the step (1). The concentration of the basic compound is preferably from 0.1 to 20 mol/liter.

The mixing and reaction temperature in the step (3) is preferably from −30 to +40° C., and more preferably from 0 to +40° C., while the residence time is preferably from 1 second to 5 hours, and more preferably from 10 minutes to 1 hour.

The aldehyde or ketone compound-containing liquid prepared in the step (3) is discharged from the step (3) and, if necessary, this liquid is subjected to an isolation step for the target compound, for example, a step such as an extraction, distillation, crystallization or silica gel column chromatography step.

A molar ratio of the sulfonyl compound to be supplied to step (1) to the primary or secondary alcohol to be supplied to step (2) is preferably within a range from 1:1 to 20:1, and more preferably from 1.1:1 to 3:1. When the molar ratio is less than 1:1, there may arise a problem such as left-over unreacted primary or secondary alcohol. On the other hand, when the molar ratio is more than 20:1, an operation of isolating an excess sulfonyl compound becomes complicated and there may arise industrial and economical problems.

When step (1) is carried out using a microreactor, the residence time of a mixed reaction solution of a sulfoxide compound-containing liquid and an activating agent-containing liquid from an inlet of a micromixer portion to an inlet of a reactor for the step (2) is preferably from 0.001 to 60 seconds, and more preferably from 0.01 to 3 seconds.

A molar ratio of the sulfonyl compound activating agent to be supplied in step (1) to the primary or secondary alcohol to be supplied in the step (2) is preferably within a range from 1:1 to 2:1, and more preferably from 1.1:1 to 1.5:1. When the molar ratio is less than 1:1, there may arise a problem such as left-over unreacted primary or secondary alcohol. On the other hand, when the molar ratio is more than 2:1, there may arise a problem that the amount of by-products increase.

A molar amount of the basic compound to be supplied to the step (3) of the method is preferably 2 to 20 times, and more preferably 2.5 to 6 times, the molar amount of the primary or secondary alcohol. When the molar amount of the basic compound is less than 2 times as that of the primary or secondary alcohol, the efficiency of the reaction of converting of the alkoxysulfonium salt into an aldehyde or ketone may become insufficient. On the other hand, when the molar amount of the basic compound is more than 20 times as that of the primary or secondary alcohol, there may arise industrial and economical problems.

The aldehyde compound or ketone compound obtained by the method corresponds to the primary alcohol or secondary alcohol used as a starting material. The following compounds can be produced by the method of the present invention:

(1) aldehydes, for example, saturated aliphatic aldehyde [for example, formaldehyde, acetoaldehyde, propionaldehyde, butylaldehyde, hexanal, higher aldehyde (octaaldehyde, nonaaldehyde, etc.)], unsaturated aliphatic aldehyde (for example, acrolein, etc.), glyoxal, methyl glyoxal, aliphatic polyaldehyde (for example, malonaldehyde, succinaldehyde, glutaraldehyde, adipinaldehyde, pimelic aldehyde, suberinaldehyde, sebacic aldehyde, etc.), aliphatic aldehyde such as aminoacetoaldehyde; aromatic aldehyde such as benzaldehyde, oxybenzaldehyde, nitrobenzaldehyde, aminobenzaldehyde, cinnamaldehyde, salicylaldehyde, anisaldehyde, 1-naphthylacetoaldehyde, vanillin (vanillaldehyde), phthalaldehyde or isophthalaldehyde, terephthalaldehyde; alicyclic aldehyde such as formylcyclohexane, citronellal or citral; heterocyclic aldehyde such as nicotinaldehyde or furfural; and (2) ketones, for example, aliphatic ketone such as acetone, methyl ethyl ketone, diethyl ketone, dipropyl ketone, methyl propyl ketone, methyl butyl ketone or pinacolone; alicyclic ketone (cyclic ketone) such as cyclopentanone, cyclohexanone, cyclooctanone, 2-methylcyclohexanone, 2-ethylcyclohexanone, 2,6-dimethylcyclohexanone, 4-chlorocyclohexanone, 4-methoxycyclohexanone, menthone or camphor; aromatic ketone such as acetophenone, propiophenone, benzophenone, deoxybenzoin or 1-naphthalenone; and heterocyclic ketone such as inden-1-one, 1,2,3-indanetrione, fluoren-9-one or 4-pyranone.

These aldehyde compounds and ketone compounds are useful in the fields of organic compound drugs and pesticides.

EXAMPLES

The method will now be described in more detail by way of the following examples.

Example 1

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two channels for respectively introducing a sulfoxide-containing liquid and an activating agent-containing liquid for the sulfoxide compound, introducing channel, a SUS tube (inner diameter: 1.0 mm, length: 20 cm) was connected, and the each channel was connected to a liquid supply source through the SUS tube.

Step (2)

A microreactor (the same as that for the step (1)) was used. A reaction product liquid discharging channel of the microreactor of the step (1) was connected to a reaction product solution-introducing channel of the microreactor of the step (2) through a connecting SUS tube (inner diameter: 0.1 mm, length: 3.2 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for the step (1)) was used.

A reaction product solution-discharging channel of the microreactor of step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound-supply source through SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor, for step (1), at a flow rate of 1.0 ml/min. Immediately after the reaction mixture solution was retained in the reactor for 0.01 seconds, the resultant reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained in the reactor for the step (2) for 1.2 seconds, the resultant reaction product solution was fed into the microreactor for the step (3) and, at the same time, a triethylamine/methylene chloride solution having a concentration of 1.4 mol/liter was fed at a flow rate of 4.0 ml/min into the reactor. After the above reaction operation was carried out for 4 minutes, the resultant reaction product solution discharged from the microreactor for the step (3) was collected in a sample bottle containing an internal standard substance for one minute.

The amount of TFAA employed in the step (1) was 1.5 equivalents, the reaction temperature of the step (1) was −20° C., and the reaction time was 0.01 seconds.

The contents of the collected compounds in the reaction product solution were determined by a gas chromatograph internal standard method. The results are shown below.

| | |
|---|---|
| Cyclohexanone | 78% |
| Cyclohexyl trifluoroacetate | 5% |
| Cyclohexyl methylthiomethyl ether | 3% |
| Cyclohexanol | 10% |

Example 2

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for sulfoxide-containing liquid and activating agent-containing liquid for the sulfoxide compound, a SUS tube (inner diameter: 1.0 mm, length: 20 cm) was connected, and the each channel was connected to a liquid supply source through the SUS tube.

Step (2)

A microreactor (the same as that for the step (1)) was used. A reaction product liquid discharging channel of the microreactor of the step (1) was connected to a reaction product solution introducing channel of a microreactor of the step (2) through a connecting SUS tube (inner diameter: 0.25 mm, length: 3.2 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of the microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of $-20°$ C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 0.05 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for step (3) and, at the same time, a triethylamine/methylene chloride solution having a concentration of 1.4 mol/liter was fed at a flow rate of 4.0 ml/min.

After the above reaction operation was carried out for 4 minutes, the reaction product solution discharged from the microreactor for the step (3) was collected in a sample bottle, containing an internal standard substance, for one minute.

The amount of TFAA employed in the step (1) was 1.5 equivalents, the reaction temperature of the step (1) was $-20°$ C., and the reaction time was 0.05 seconds.

The contents of the collected compounds in the reaction product solution were determined by a gas chromatograph internal standard method. The results are shown below.

| | |
|---|---|
| Cyclohexanone | 66% |
| Cyclohexyl trifluoroacetate | 6% |
| Cyclohexyl methylthiomethyl ether | 5% |
| Cyclohexanol | 21% |

Example 3

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as that for the step (1)) was used. A reaction product liquid discharging channel of the microreactor of the step (1) was connected to a reaction product solution-introducing channel of a microreactor of the step (2) through a connecting SUS tube (inner diameter: 1.0 mm, length: 10 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution discharging channel of the microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution discharging channel.

The microreactors for the steps (1), (2) and (3) and the SUS tubes connected thereto were dipped in a constant low temperature bath set at a temperature of $-20°$ C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm)

made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the resultant reaction product solution discharged from the microreactor for the step (3) was collected in a sample bottle containing an internal standard substance for one minute.

The amount of TFAA employed in the step (1) was 1.5 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 66% |
| Cyclohexyl trifluoroacetate | 6% |
| Cyclohexyl methylthiomethyl ether | 5% |
| Cyclohexanol | 18% |

Example 4

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as that for the step (1)) was used. A reaction product liquid discharging channel of the microreactor of the step (1) was connected to a reaction product solution introducing channel of a microreactor of the step (2) through a connecting SUS tube (inner diameter: 1.0 mm, length: 100 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution discharging channel of the microreactor of the step (2) was connected to a reaction product solution introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution discharging channel.

The microreactors for the steps (1), (2) and (3) and the SUS tubes connected thereto were dipped in a constant low temperature bath set at a temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min, through a gas-tight syringe. Immediately after the reaction mixture solution was retained for 24 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution discharged from the microreactor for the step (3) was collected in a sample bottle, containing an internal standard substance, for one minute.

The amount of TFAA employed in the step (1) was 1.5 equivalents, the reaction temperature of the step (1) was −20° C., and the reaction time was 24 seconds.

The contents of the collected compounds in the reaction product solution were determined by a gas chromatograph internal standard method. The results are shown below.

| | |
|---|---|
| Cyclohexanone | 70% |
| Cyclohexyl trifluoroacetate | 5% |
| Cyclohexyl methylthiomethyl ether | 6% |
| Cyclohexanol | 15% |

Example 5

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as that for step (1)) was used. A reaction product liquid discharging channel of the microreactor of the step (1) was connected to a reaction product solution-introducing channel of a microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for step (3) through a connecting SUS tube (inner diameter: 1.0 mm, length: 100 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low temperature bath set at a temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 12 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution discharged from the microreactor for the step (3) was collected in a sample bottle, containing an internal standard substance, for one minute.

The amount of TFAA employed in the step (1) was 1.5 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 71% |
| Cyclohexyl trifluoroacetate | 5% |
| Cyclohexyl methylthiomethyl ether | 6% |
| Cyclohexanol | 15% |

Example 6

In the production of cyclohexanone from cyclohexanol by the method, the steps (1), (2) and (3) were carried out using the following reactor.

Step (1)

T-shaped joint-type reactor (cross-sectional inner diameter: 0.8 mm)

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source, through the SUS tube.

Step (2)

A microreactor (manufactured by IMM GmbH, Single Mixer Ver. 2, Inlay: Ag plating, fine liquid-introducing channel width: 40 μm) was used. A reaction product liquid-discharging channel of the T joint type reactor of the step (1) was connected to a reaction product solution introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (2)) was used.

A reaction product solution-discharging channel of a microreactor of the step (2) was connected to a reaction product solution introducing channel for the step (3) through a connecting SUS tube (inner diameter: 1.0 mm, length: 10 cm). Also, a basic compound introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low temperature bath set at a temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution discharged from the microreactor for the step (3) was collected in a sample bottle, containing an internal standard substance, for one minute.

The amount of TFAA employed in the step (1) was 1.5 equivalents, the reaction temperature of the step (1) was −20° C., and the reaction time was 2.4 seconds.

The contents of the collected compounds in the reaction product solution were determined by a gas chromatograph internal standard method. The results are shown below.

| Cyclohexanone | 72% |
|---|---|
| Cyclohexyl trifluoroacetate | 10% |
| Cyclohexyl methylthiomethyl ether | 3% |
| Cyclohexanol | 8% |

Example 7

In the production of cyclohexanone from cyclohexanol by the method, the steps (1), (2) and (3) were carried out using the following reactors.

Step (1)

A microreactor (manufactured by IMM GmbH, Single Mixer Ver. 2, Inlay: Ag plating, fine liquid-introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A T-joint-type reactor (cross-sectional inner diameter: 0.8 mm) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol introducing-channel of a microreactor for step (2) through a SUS tube (inner diameter: 1.0 mm, length: 20 cm).

Step (3)

A microreactor (the same as microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA used in the step (1) was 1.5 equivalents, the reaction temperature of the step (1) was −20° C., and the reaction time was 2.4 seconds.

The contents of the collected compounds in the reaction product solution were determined by a gas chromatograph internal standard method. The results are shown below.

| Cyclohexanone | 55% |
|---|---|
| Cyclohexyl trifluoroacetate | 24% |
| Cyclohexyl methyithiomethyl ether | 4% |
| Cyclohexanol | 15% |

Example 8

In the production of cyclohexanone from cyclohexanol by the method, the steps (1), (2) and (3) were carried out using the reactors shown below.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter:

1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A T-joint-type reactor (cross-sectional inner diameter: 0.8 mm) was used. A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the resultant reaction product solution discharged from the microreactor for the step (3) was collected in a sample bottle, containing an internal standard substance, for one minute.

The amount of TFAA used in the step (1) was 1.5 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 69% |
| Cyclohexyl trifluoroacetate | 7% |
| Cyclohexyl methylthiomethyl ether | 5% |
| Cyclohexanol | 19% |

Example 9

In the production of cyclohexanone from cyclohexanol by the method, the steps (1), (2) and (3) were carried out using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A T-joint-type reactor (cross-sectional inner diameter: 0.8 mm) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in the step (1) was 1.2 equivalents, the reaction temperature of the step (1) was −20° C., and the reaction time was 2.4 seconds.

The contents of the collected compounds in the reaction product solution were determined by a gas chromatograph internal standard method. The results are shown below.

| Cyclohexanone | 63% |
| Cyclohexyl trifluoroacetate | 22% |
| Cyclohexyl methylthiomethyl ether | 4% |
| Cyclohexanol | 9% |

Example 10

In the production of cyclohexanone from cyclohexanol by the method, the steps (1), (2) and (3) were carried out using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for step (3) and, at the same time, a triethylamine/methylene chloride solution having a concentration of 1.5 mol/liter was fed at a flow rate of 4.0 ml/min. After the above reaction operation was carried out for 4 minutes, the reaction product solution discharged from the microreactor for the step (3) was collected in a sample bottle, containing an internal standard substance, for one minute.

The amount of TFAA employed in the step (1) was 1.0 equivalents, the reaction temperature of the step (1) was −20° C., and the reaction time was 2.4 seconds.

The contents of the collected compounds in the reaction product solution were determined by a gas chromatograph internal standard method. The results are shown below.

| Cyclohexanone | 67% |
| Cyclohexyl trifluoroacetate | 1% |
| Cyclohexyl methylthiomethyl ether | 4% |
| Cyclohexanol | 23% |

Example 11

In the production of cyclohexanone from cyclohexanol by the method, the steps (1), (2) and (3) were carried out using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of step (2) through a connecting SUS tube (inner diameter: 1.0 mm, length: 10 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) using a connecting SUS tube (inner diameter: 1.0 mm, length: 10 cm). Also, a basic compound introducing channel of a microreactor for the step (3) was connected to a basic compound supply source through a SUS tube (inner diameter: 1.0 mm, length: 20 cm) and then a reaction product solution discharging SUS tube (inner diameter: 1.0 mm, length: 20 cm) was connected to a reaction product solution discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide (DMSO)/methylene chloride solution having a concentration of 2.0 mol/liter and a trifluoroacetic anhydride (TFAA)/methylene chloride solution having a concentration of 2.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for the step (3) and was collected in a sample bottle containing an internal standard substance for one minute.

The amount of DMSO and TFAA used in the step (1) was 1.0 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 69% |
| Cyclohexyl trifluoroacetate | 5% |
| Cyclohexyl methylthiomethyl ether | 4% |
| Cyclohexanol | 17% |

Example 12

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 3.0 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in the step (1) was 1.2 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 74% |
| Cyclohexyl trifluoroacetate | 2% |
| Cyclohexyl methylthiomethyl ether | 4% |
| Cyclohexanol | 15% |

Example 13

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid-introducing channel and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as microreactor for the step (1)) was used.

A reaction product solution-discharging channel of a microreactor of step (2) was connected to a reaction product solution-introducing channel for step (3) through a connecting SUS tube (inner diameter: 1.0 mm, length: 10 cm). Also, a basic compound introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution discharging channel.

The microreactors for steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 0.8 mol/liter and a trifluoroacetic anhydride (TFAA)/methylene chloride solution having a concentration of 0.5 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 0.2 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 0.3 mol/liter was fed at a flow rate of 4.0 ml/min. After the above reaction operation was carried out for 4 minutes, the reaction product solution was discharged from the microreactor for step (3) and was collected in a sample bottle, containing an internal standard substance, for one minute.

The amount of TFAA employed in step (1) was 1.2 equivalents, the reaction temperature of the step (1) was −20° C., and the reaction time was 2.4 seconds.

The contents of the collected compounds in the reaction product solution was determined by a gas chromatograph internal standard method. The results are shown below.

| | |
|---|---|
| Cyclohexanone | 84% |
| Cyclohexyl trifluoroacetate | 4% |
| Cyclohexyl methylthiomethyl ether | 5% |
| Cyclohexanol | 9% |

Example 14

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution discharging channel.

The microreactors for the steps (1), (2) and (3) and the SUS tubes connected thereto were dipped in a constant low-temperature bath set at a constant temperature of 0° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.4 mol/liter was fed at a flow rate of 4.0 ml/min. After the above reaction operation was carried out for 4 minutes, the reaction product solution was discharged from the microreactor for step (3) and was collected in a sample bottle, containing an internal standard substance, for one minute.

The amount of TFAA employed in the step (1) was 1.5 equivalents, the reaction temperature of the step (1) was 0° C., and the reaction time was 2.4 seconds.

The contents of the collected compounds in the reaction product solution were determined by a gas chromatograph internal standard method. The results are shown below.

| | |
|---|---|
| Cyclohexanone | 36% |
| Cyclohexyl trifluoroacetate | 9% |
| Cyclohexyl methylthiomethyl ether | 2% |
| Cyclohexanol | 48% |

Example 15

In the production of decanal from decanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and the each channel was connected to a liquid supply source through the SUS tube.

Step (2)

A microreactor (the same as the microreactor for step (1)) was used. A reaction product liquid discharging channel of the microreactor of the step (1) was connected to a reaction product solution introducing channel of the microreactor of the step (2) through a connecting SUS tube (inner diameter: 1.0 mm, length: 10 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution discharging-channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for step (1) at a flow rate of 1.0 ml/min. Immediately after the reaction mixture solution was retained for 2.4 seconds, the reaction product solution was fed into the microreactor for the step (2) and, at the same time, a decanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in the step (1) was 1.2 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Decanal | 71% |
| Decyl trifluoroacetate | 18% |
| Decyl methylthiomethyl ether | 8% |
| Decanol | 5% |

Example 16

In the production of 2-octanone from 2-octanol by the method, the steps (1), (2) and (3) were carried out using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source, through the SUS tube.

Step (2)

A microreactor (the same as the microreactor for step (1)) was used. A reaction product liquid-discharging channel of the microreactor of step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected using a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a 2-octanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in step (1) was 1.2 equivalents, the reaction temperature of step (1) was −20° C., and the reaction time was 2.4 seconds.

The contents of the collected compounds in the reaction product solution were determined by a gas chromatograph internal standard method. The results are shown below.

| | |
|---|---|
| 2-octanone | 87% |
| Octyl trifluoroacetate | 2% |
| Octyl methylthiomethyl ether | 5% |
| 2-octanol | 8% |

Example 17

In the production of cyclohexanone from cyclohexanol by the method, the steps (1), (2) and (3) were carried out using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel for the step (3) through a connecting SUS tube (inner diameter: 1.0 mm, length: 10 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 2.4 seconds, the reaction product solution was fed into the microreactor for step (2) and, at the same time, a cyclohexanol/methylene chloride solution having a concentration of 1.0 mol/liter was fed into the microreactor for step (2) at a flow rate of 2.0 ml/min. Immediately after the reaction mixture solution was retained for 1.2 seconds, the reaction product solution was fed into the microreactor for step (3) and, at the same time, a triethylamine/methylene chloride solution having a concentration of 1.4 mol/liter was fed at a flow rate of 4.0 ml/min. After the above reaction operation was carried out for 4 minutes, the reaction product solution was discharged from the microreactor for the step (3) and was collected in a sample bottle containing an internal standard substance for one minute.

The amount of TFAA employed in the step (1) was 1.2 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Cyclohexanone | 77% |
| Cyclohexyl trifluoroacetate | 4% |
| Cyclohexyl methylthiomethyl ether | 5% |
| Cyclohexanol | 12% |

Example 18

In the production of benzaldehyde from benzyl alcohol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 2.4 seconds, the reaction product solution was fed into the microreactor for the step (2) and, at the same time, a benzyl alcohol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in the step (1) was 1.2 equivalents, the reaction temperature of the step (1) was −20° C., and the reaction time was 2.4 seconds.

The contents of the collected compounds in the reaction product solution were determined by a gas chromatograph internal standard method. The results are shown below.

| | |
|---|---|
| Benzaldehyde | 88% |
| Benzyl trifluoroacetate | 8% |
| Benzyl alcohol | 3% |

Example 19

In the production of cyclohexanone from cyclohexanol by the method, the steps (1), (2) and (3) were carried out by using the following reactors.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 0.1 mm, length: 3.2 cm), and then an alcohol supply source was connected to an alcohol-introducing channel of the microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for step (1) at a flow rate of 1.0 ml/min. Immediately after the reaction mixture solution was retained for 0.01 seconds, the reaction product solution was fed into the microreactor for step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for step (3) and was collected in a sample bottle, containing an internal standard substance, for one minute.

The amount of TFAA employed in the step (1) was 1.2 equivalents, the reaction temperature of the step (1) was −20° C., and the reaction time was 0.01 seconds.

The contents of the collected compounds in the reaction product solution were determined by a gas chromatograph internal standard method. The results are shown below.

| | |
|---|---|
| Cyclohexanone | 75% |
| Cyclohexyl trifluoroacetate | 1% |
| Cyclohexyl methylthiomethyl ether | 6% |
| Cyclohexanol | 15% |

Example 20

In the production of cyclohexanone from cyclohexanol by the method, the steps (1), (2) and (3) were carried out by using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of step (2) using a connecting SUS tube (inner diameter: 0.1 mm, length: 3.2 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of 0° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 0.01 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for the step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for step (3) and was collected in a sample bottle, containing an internal standard substance, for one minute.

The amount of TFAA employed in the step (1) was 1.2 equivalents, the reaction temperature of the step (1) was 0° C., and the reaction time was 0.01 seconds.

The contents of the collected compounds in the reaction product solution were determined by a gas chromatograph internal standard method. The results are shown below.

| | |
|---|---|
| Cyclohexanone | 80% |
| Cyclohexyl trifluoroacetate | 1% |
| Cyclohexyl methylthiomethyl ether | 6% |
| Cyclohexanol | 10% |

Example 21

In the production of cyclohexanone from cyclohexanol by the method, the steps (1), (2) and (3) were carried out by using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 0.1 mm, length: 3.2 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel for step (3) through a connecting SUS tube (inner diameter: 1.0 mm, length: 10 cm). Also, a basic compound introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of 20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for the step (1) at a flow rate of 1.0 ml/min. Immediately after the reaction mixture solution was retained for 0.01 seconds, the reaction product solution was fed into the microreactor for the step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for step (3) and, at the same time, a triethylamine/methylene chloride solution having a concentration of 1.4 mol/liter was fed at a flow rate of 4.0 ml/min. After the above reaction operation was carried out for 4 minutes, the reaction product solution was discharged from the microreactor for step (3) and was collected in a sample bottle, containing an internal standard substance, for one minute.

The amount of TFAA employed in the step (1) was 1.2 equivalents, the reaction temperature of the step (1) was 20° C., and the reaction time was 0.01 seconds.

The contents of the collected compounds in the reaction product solution were determined by a gas chromatograph internal standard method. The results are shown below.

| | |
|---|---|
| Cyclohexanone | 71% |
| Cyclohexyl trifluoroacetate | 2% |
| Cyclohexyl methylthiomethyl ether | 4% |
| Cyclohexanol | 19% |

Example 22

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter:

1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as microreactor for the step (1)) was used.

A reaction product solution-discharging channel of a microreactor of step (2) was connected to a reaction product solution-introducing channel for step (3) through a connecting SUS tube (inner diameter: 1.0 mm, length: 10 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of 0° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 2.4 mol/liter were respectively fed into the microreactor for step (1) at a flow rate of 1.0 ml/min. Immediately after the reaction mixture solution was retained for 2.3 seconds, the reaction product solution was fed into the microreactor for step (2) and, at the same time, a cyclohexanol/methylene chloride solution having a concentration of 1.0 mol/liter was fed into the microreactor for the step (2) at a flow rate of 2.0 ml/min. Immediately after the reaction mixture solution was retained for 1.2 seconds, the reaction product solution was fed into the microreactor for step (3) and, at the same time, a triethylamine/methylene chloride solution having a concentration of 1.5 mol/liter was fed at a flow rate of 4.0 ml/min. After the above reaction operation was carried out for 4 minutes, the reaction product solution was discharged from the microreactor for the step (3) and was collected in a sample bottle, containing an internal standard substance, for one minute.

The amount of TFAA employed in the step (1) was 1.2 equivalents, the reaction temperature of the step (1) was 0° C., and the reaction time was 2.4 seconds.

The contents of the collected compounds in the reaction product solution were determined by a gas chromatograph internal standard method. The results are shown below.

| | |
|---|---|
| Cyclohexanone | 32% |
| Cyclohexyl trifluoroacetate | 7% |
| Cyclohexyl methylthiomethyl ether | 3% |
| Cyclohexanol | 50% |

Example 23

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of the step (2) through a connecting SUS tube (inner diameter: 0.25 mm, length: 3.2 cm), and then an alcohol supply source was connected to an alcohol-introducing channel of a microreactor for step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C.

By using a gas-tight syringe, a dimethyl sulfoxide/methylene chloride solution having a concentration of 2.0 mol/liter was fed into the microreactor for step (1) at a flow rate of 4.0 ml/min and a trifluoroacetic anhydride (TFAA)/methylene chloride solution having a concentration of 3.0 mol/liter were respectively fed into the microreactor for the step (1) at a flow rate of 2.0 ml/min. Immediately after the reaction mixture solution was retained for 0.02 seconds, the reaction product solution was fed into the microreactor for the step (2) and, at the same time, a cyclohexanol/methylene chloride solution having a concentration of 2.0 mol/liter was fed into the microreactor for the step (2) at a flow rate of 2.0 ml/min. Immediately after the reaction mixture solution was retained for 0.6 seconds, the reaction product solution was fed into the microreactor for the step (3) and, at the same time, triethylamine was fed at a flow rate of 1.6 ml/min. After the above reaction operation was carried out for 4 minutes, the reaction product solution was discharged from the microreactor for the step (3) and was collected in a sample bottle, containing an internal standard substance, for one minute.

The contents of the collected compounds in the reaction product solution was determined by a gas chromatograph internal standard method. The results are shown below.

| | |
|---|---|
| Cyclohexanone | 55% |
| Cyclohexyl trifluoroacetate | 9% |
| Cyclohexyl methylthiomethyl ether | 7% |
| Cyclohexanol | 27% |

Example 24

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid discharging channel of the microreactor of the step (1) was connected to a reaction product solution introducing channel of the microreactor of the step (2) through a connecting SUS tube (inner diameter: 1.0 mm, length: 10 cm), and then an alcohol supply source was connected to an alcohol introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel for step (3) through a connecting SUS tube (inner diameter: 1.0 mm, length: 10 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C.

By using a gas-tight syringe, a dimethyl sulfoxide/methylene chloride solution having a concentration of 2.0 mol/liter was fed into the microreactor for step (1) at a flow rate of 4.0 ml/min and a trifluoroacetic anhydride (TFAA)/methylene chloride solution having a concentration of 3.0 mol/liter were respectively fed into the microreactor for step (1) at a flow rate of 2.0 ml/min. Immediately after the reaction mixture solution was retained for 0.8 seconds, the reaction product solution was fed into the microreactor for step (2) and, at the same time, a cyclohexanol/methylene chloride solution having a concentration of 2.0 mol/liter was fed into the microreactor for the step (2) at a flow rate of 2.0 ml/min. Immediately after the reaction mixture solution was retained for 0.6 seconds, the reaction product solution was fed into the microreactor for the step (3) and, at the same time, triethylamine was fed at a flow rate of 1.6 ml/min.

After the above reaction operation was carried out for 4 minutes, the reaction product solution was discharged from the microreactor for the step (3) and was collected in a sample bottle containing an internal standard substance for one minute.

The contents of the collected compounds in the reaction product solution were determined by a gas chromatograph internal standard method. The results are shown below.

| | |
|---|---|
| Cyclohexanone | 60% |
| Cyclohexyl trifluoroacetate | 7% |
| Cyclohexyl methylthiomethyl ether | 7% |
| Cyclohexanol | 23% |

Example 25

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution-introducing channel of the microreactor of the step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution introducing channel for the step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −30° C.

By using a gas-tight syringe, a dimethyl sulfoxide/methylene chloride solution having a concentration of 2.0 mol/liter was fed into the microreactor for step (1) at a flow rate of 4.0 ml/min and a trifluoroacetic anhydride (TFAA)/methylene chloride solution having a concentration of 3.0 mol/liter was fed into the microreactor for step (1) at a flow rate of 2.0 ml/min. Immediately after the reaction mixture solution was retained for 0.8 seconds, the reaction product solution was fed into the microreactor for step (2) and, at the same time, a cyclohexanol/methylene chloride solution having a concentration of 2.0 mol/liter was fed into the microreactor for step (2) at a flow rate of 2.0 ml/min. Immediately after the reaction mixture solution was retained for 0.6 seconds, the reaction product solution was fed into the microreactor for step (3) and, at the same time, triethylamine was fed at a flow rate of 1.6 ml/min. After the above reaction operation was carried out for 4 minutes, the reaction product solution was discharged from the microreactor for step (3) and was collected in a sample bottle, containing an internal standard substance, for one minute.

The contents of the collected compounds in the reaction product solution were determined by a gas chromatograph internal standard method. The results are shown below.

| Cyclohexanone | 58% |
|---|---|
| Cyclohexyl trifluoroacetate | 11% |
| Cyclohexyl methylthiomethyl ether | 9% |
| Cyclohexanol | 21% |

Example 26

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of step (2) using a connecting SUS tube (inner diameter: 1.0 mm, length: 10 cm), and then an alcohol supply source was connected to an alcohol-introducing channel of a microreactor for step (2) through a SUS tube (inner diameter: 1.0 mm, length: 20 cm).

Step (3)

A microreactor (the same as the microreactor for step (1)) was used.

A reaction product solution-discharging channel of a microreactor of the step (2) was connected to a reaction product solution-introducing channel of the microreactor for the step (3) through a connecting SUS tube (inner diameter: 0.25 mm, length: 3.2 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C.

By using a gas-tight syringe, a dimethyl sulfoxide/methylene chloride solution having a concentration of 2.0 mol/liter was fed into the microreactor for step (1) at a flow rate of 4.0 ml/min and a trifluoroacetic anhydride (TFAA)/methylene chloride solution having a concentration of 3.0 mol/liter was fed into the microreactor for step (1) at a flow rate of 2.0 ml/min. Immediately after the reaction mixture solution was retained for 0.8 seconds, the reaction product solution was fed into the microreactor for step (2) and, at the same time, a cyclohexanol/methylene chloride solution having a concentration of 2.0 mol/liter was fed into the microreactor for step (2) at a flow rate of 2.0 ml/min. Immediately after the reaction mixture solution was retained for 0.01 seconds, the reaction product solution was fed into the microreactor for the step (3) and, at the same time, triethylamine was fed at a flow rate of 1.6 ml/min. After the above reaction operation was carried out for 4 minutes, the reaction product solution was discharged from the microreactor for the step (3) and was collected in a sample bottle, containing an internal standard substance, for one minute.

The contents of the collected compounds in the reaction product solution were determined by a gas chromatograph internal standard method. The results are shown below.

| Cyclohexanone | 52% |
|---|---|
| Cyclohexyl trifluoroacetate | 10% |
| Cyclohexyl methylthiomethyl ether | 6% |
| Cyclohexanol | 29% |

Example 27

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as microreactor for the step (1)) was used. A reaction product liquid-discharging channel of the microreactor of step (1) was connected to a reaction product solution-introducing channel of the microreactor of step (2) through a connecting SUS tube (inner diameter: 1.0 mm, length: 10 cm), and then an alcohol supply source was connected to an alcohol-introducing channel of a microreactor for the step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel for step (3) using a connecting SUS tube (inner diameter: 1.0 mm, length: 30 cm). Also, a basic compound-introducing channel of a microreactor for step (3) was connected to a basic compound supply source through a SUS tube (inner diameter: 1.0 mm, length: 20 cm)

and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C.

By using a gas-tight syringe, a dimethyl sulfoxide/methylene chloride solution having a concentration of 2.0 mol/liter was fed into the microreactor for the step (1) at a flow rate of 4.0 ml/min and a trifluoroacetic anhydride (TFAA)/methylene chloride solution having a concentration of 3.0 mol/liter was fed into the microreactor for step (1) at a flow rate of 2.0 ml/min. Immediately after the reaction mixture solution was retained for 0.8 seconds, the reaction product solution was fed into the microreactor for step (2) and, at the same time, a cyclohexanol/methylene chloride solution having a concentration of 2.0 mol/liter was fed into the microreactor for step (2) at a flow rate of 2.0 ml/min. Immediately after the reaction mixture solution was retained for 1.8 seconds, the reaction product solution was fed into the microreactor for step (3) and, at the same time, triethylamine was fed at a flow rate of 1.6 ml/min. After the above reaction operation was carried out for 4 minutes, the reaction product solution was discharged from the microreactor for step (3) and was collected in a sample bottle, containing an internal standard substance, for one minute.

The contents of the collected compounds in the reaction product solution were determined by a gas chromatograph internal standard method. The results are shown below.

| | |
|---|---|
| Cyclohexanone | 64% |
| Cyclohexyl trifluoroacetate | 6% |
| Cyclohexyl methylthiomethyl ether | 7% |
| Cyclohexanol | 23% |

Example 28

In the production of cyclohexanone from cyclohexanol by the method, the steps (1), (2) and (3) were carried out using the following reactor.

Step (1)

A microreactor (manufactured by IMM CO., Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of the step (1) was connected to a reaction product solution introducing channel of the microreactor of the step (2) through a connecting SUS tube (inner diameter: 1.0 mm, length: 10 cm), and then an alcohol supply source was connected to an alcohol-introducing channel of a microreactor for step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel of the microreactor for step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C.

By using a gas-tight syringe, a dimethyl sulfoxide/methylene chloride solution having a concentration of 2.2 mol/liter was fed into the microreactor for step (1) at a flow rate of 1.0 ml/min and a trifluoroacetic anhydride (TFAA)/methylene chloride solution having a concentration of 2.1 mol/liter was fed into the microreactor for step (1) at a flow rate of 1.0 ml/min. Immediately after the reaction mixture solution was retained for 2.4 seconds, the reaction product solution was fed into the microreactor for step (2) and, at the same time, a cyclohexanol/methylene chloride solution having a concentration of 1.0 mol/liter was fed into the microreactor for step (2) at a flow rate of 2.0 ml/min. Immediately after the reaction mixture solution was retained for 1.2 seconds, the reaction product solution was fed into the microreactor for the step (3) and, at the same time, triethylamine was fed at a flow rate of 0.8 ml/min. After the above reaction operation was carried out for 4 minutes, the reaction product solution was discharged from the microreactor for step (3) and was collected in a sample bottle, containing an internal standard substance, for one minute.

The contents of the collected compounds in the reaction product solution were determined by a gas chromatograph internal standard method. The results are shown below.

| | |
|---|---|
| Cyclohexanone | 63% |
| Cyclohexyl trifluoroacetate | 6% |
| Cyclohexyl methylthiomethyl ether | 6% |
| Cyclohexanol | 22% |

Example 29

In the production of cyclohexanone from cyclohexanol by the method, the steps (1), (2) and (3) were carried out using the following reactor.

Step (1)

A microreactor (manufactured by IMM GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of step (2) through a connecting SUS tube (inner diameter: 1.0 mm, length: 10 cm), and then an alcohol supply source was connected to an alcohol-introducing channel of a microreactor for step (2) using a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution introducing channel for step (3) through a connecting SUS tube (inner diameter: 1.0 mm, length: 10 cm). Also, a basic compound-introducing channel of a microreactor for step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 2.2 mol/liter was fed into the microreactor for step (1) at a flow rate of 1.0 ml/min and a trifluoroacetic anhydride (TFAA)/methylene chloride solution having a concentration of 2.1 mol/liter was fed into the microreactor for step (1) at a flow rate of 1.0 ml/min. Immediately after the reaction mixture solution was retained for 2.4 seconds, the reaction product solution was fed into the microreactor for step (2) and, at the same time, a cyclohexanol/methylene chloride solution having a concentration of 1.0 mol/liter was fed into the microreactor for step (2) at a flow rate of 2.0 ml/min. Immediately after the reaction mixture solution was retained for 1.2 seconds, the reaction product solution was fed into the microreactor for step (3) and, at the same time, triethylamine was fed at a flow rate of 0.8 ml/min. After the above reaction operation was carried out for 4 minutes, the reaction product solution was discharged from the microreactor for the step (3) and was collected in a sample bottle, containing an internal standard substance, for one minute.

The contents of the collected compounds in the reaction product solution were determined by a gas chromatograph internal standard method. The results are shown below.

| | |
|---|---|
| Cyclohexanone | 60% |
| Cyclohexyl trifluoroacetate | 8% |
| Cyclohexyl methylthiomethyl ether | 5% |
| Cyclohexanol | 24% |

Example 30

In the production of cyclohexanone from cyclohexanol by the method, the steps (1), (2) and (3) were carried out using the following reactor.

Step (1)

A microreactor (manufactured by GmbH, Single Mixer Ver. 2, Inlay: Ag plating, fine liquid introducing channel width: 40 μm) was used.

To each of two introduction channels for a sulfoxide-containing liquid and an activating agent-containing liquid for the sulfoxide compound, a SUS tube (inner diameter: 1.0 mm, length: 20 cm) was connected, and each channel was connected to a liquid supply source through the SUS tube.

Step (2)

A microreactor (the same as the microreactor for step (1)) was used. A reaction product liquid-discharging channel of the microreactor of step (1) was connected to a reaction product solution-introducing channel of the microreactor of step (2) through a connecting SUS tube (inner diameter: 1.0 mm, length: 10 cm), and then an alcohol supply source was connected to an alcohol-introducing channel of a microreactor for step (2) through a SUS tube (inner diameter: 1.0 mm, length: 20 cm).

Step (3)

A microreactor (the same as the microreactor for step (1)) was used.

A reaction product solution-discharging channel of a microreactor of step (2) was connected to a reaction product solution-introducing channel of the microreactor for step (3) through a connecting SUS tube (inner diameter: 1.0 mm, length: 10 cm). Also, a basic compound-introducing channel of a microreactor for the step (3) was connected to a basic compound supply source through a SUS tube (inner diameter: 1.0 mm, length: 20 cm) and then a reaction product solution-discharging SUS tube (inner diameter: 1.0 mm, length: 20 cm) was connected to a reaction product solution-discharging channel.

The microreactors for the steps (1), (2) and (3) and the SUS tubes connected thereto were dipped in a constant low-temperature bath set at a constant temperature of −20° C. To the end of the SUS tube for discharging a reaction product solution of the microreactor for the step (3), a SUS tube (inner diameter: 1.0 mm, length: 100 cm) was connected through a connecting tube (inner diameter: 1 mm, length: 50 cm) made of PTFE (polytetrafluoroethylene), and then only the connecting tube was dipped in a water bath at a temperature of 30° C.

By using a gas-tight syringe, a dimethyl sulfoxide/methylene chloride solution having a concentration of 4.0 mol/liter and a trifluoroacetic anhydride (TFAA)/methylene chloride solution having a concentration of 3.0 mol/liter were respectively fed into the microreactor for step (1) at a flow rate of 1.0 ml/min, respectively. Immediately after the reaction mixture solution was retained for 2.4 seconds, the reaction product solution was fed into the microreactor for step (2) and, at the same time, a cyclohexanol/methylene chloride solution having a concentration of 1.0 mol/liter was fed into the microreactor for step (2) at a flow rate of 2.0 ml/min. Immediately after the reaction mixture solution was retained for 1.2 seconds, the reaction product solution was fed into the microreactor for step (3) and, at the same time, triethylamine was fed at a flow rate of 0.8 ml/min. After the above reaction operation was carried out for 4 minutes, the reaction product solution was discharged from the microreactor for the step (3) and was collected in a sample bottle, containing an internal standard substance, for one minute.

The contents of the collected compounds in the reaction product solution were determined by a gas chromatograph internal standard method. The results are shown below.

| | |
|---|---|
| Cyclohexanone | 62% |
| Cyclohexyl trifluoroacetate | 6% |
| Cyclohexyl methylthiomethyl ether | 8% |
| Cyclohexanol | 21% |

Comparative Example 1 (Batch Synthesis Comparative Example)

In an argon gas atmosphere, 1 ml of a dimethyl sulfoxide/methylene chloride solution having a concentration of 4 mol/liter was charged in a Schrenk tube having an inner volume of 30 ml and then cooled to a temperature of −23° C. While stirring this solution by using a magnetic stirrer, 1 ml of a trifluoroacetic anhydride/methylene chloride solution having a concentration of 2.4 mol/liter was added dropwise to the solution at an addition rate of 0.1 ml/min, followed by mixing.

After the completion of the dropwise addition and mixing, the resultant mixture solution was stirred at the above temperature for 10 minutes. To this mixture solution, 2 ml of a decanol/methylene chloride solution having a concentration of 1.0 mol/liter was added dropwise at an addition rate of 0.2 ml/min, followed by mixing.

After the completion of the dropwise addition and mixing, the resultant mixture solution was stirred at the above-mentioned temperature for 10 minutes. To the resultant mixture solution, 4 ml of a triethylamine/methylene chloride solution having a concentration of 1.5 mol/liter was added dropwise at an addition rate of 0.4 ml/min, followed by mixing.

After the completion of the dropwise addition and mixing, the temperature of the resultant mixture solution was returned to room temperature and an internal standard agent was added thereto, and then the contents of the compounds in the mixture solution were measured by a gas chromatograph internal standard method. The measurement results are shown below.

| | |
|---|---|
| Decanal | 8% |
| Decyl trifluoroacetate | 66% |
| Decyl methylthiomethyl ether | 1% |
| Decanol | 27% |

Comparative Example 2 (Batch Synthesis Comparative Example)

In an argon gas atmosphere, 1 ml of a dimethyl sulfoxide/methylene chloride solution having a concentration of 4 mol/liter was charged in a Schrenk tube having an inner volume of 30 ml and then cooled to a temperature of −23° C. While stirring this solution using a magnetic stirrer, 1 ml of a trifluoroacetic anhydride/methylene chloride solution having a concentration of 2.4 mol/liter was added dropwise to the solution at an addition rate of 0.1 ml/min, followed by mixing.

After the completion of the dropwise addition and mixing, the resultant mixture solution was stirred at the above temperature for 10 minutes. To this mixture solution, 2 ml of a 2-octanol/methylene chloride solution having a concentration of 1.0 mol/liter was added dropwise at an addition rate of 0.2 ml/min, followed by mixing.

After the completion of the dropwise addition and mixing, the resultant mixture solution was stirred at the above temperature for 10 minutes. To the resultant mixture solution, 4 ml of a triethylamine/methylene chloride solution having a concentration of 1.5 mol/liter was added dropwise at an addition rate of 0.4 ml/min, followed by mixing.

After the completion of the dropwise addition and mixing, the temperature of the resultant mixture solution was returned to room temperature and an internal standard agent was added thereto, and then the contents of the compounds in the mixed solution were measured by a gas chromatograph internal standard method. The measurement results are shown below.

| | |
|---|---|
| 2-octanone | 10% |
| Octyl trifluoroacetate | 38% |
| Octyl methylthiomethyl ether | 1% |
| 2-octanol | 49% |

Comparative Example 3 (Batch Synthesis Comparative Example)

In an argon gas atmosphere, 2 ml of a dimethyl sulfoxide/methylene chloride solution having a concentration of 4 mol/liter was charged in a Schrenk tube having an inner volume of 30 ml and then cooled to a temperature of −27° C. While stirring this solution using a magnetic stirrer, 2 ml of a trifluoroacetic anhydride/methylene chloride solution having a concentration of 3.0 mol/liter was added dropwise to the solution at an addition rate of 0.2 ml/min, followed by mixing.

After the completion of the dropwise addition and mixing, the resultant mixture solution was stirred at the above temperature for 10 minutes. To this mixed solution, 4 ml of a cyclohexanol/methylene chloride solution having a concentration of 1.0 mol/liter was added dropwise at an addition rate of 0.4 ml/min, followed by mixing.

After the completion of the dropwise addition and mixing, the resultant mixture solution was stirred at the above temperature for 10 minutes. To the resulting mixed solution, 8 ml of a triethylamine/methylene chloride solution having a concentration of 1.4 mol/liter was added dropwise at an addition rate of 0.8 ml/min, followed by mixing.

After the completion of the dropwise addition and mixing, the temperature of the resultant mixture solution was returned to room temperature and an internal standard agent was added thereto, and then the contents of the compounds in the mixed solution were measured by a gas chromatograph internal standard method. The measurement results are shown below.

| | |
|---|---|
| Cyclohexanone | 45% |
| Cyclohexyl trifluoroacetate | 11% |
| Cyclohexyl methylthiomethyl ether | 5% |
| Cyclohexanol | 36% |

Comparative Example 4 (Batch Synthesis Comparative Example)

In an argon gas atmosphere, 1 ml of a dimethyl sulfoxide/methylene chloride solution having a concentration of 4 mol/liter was charged in a Schrenk tube having an inner volume of 30 ml and then cooled to a temperature of −23° C. While stirring this solution using a magnetic stirrer, 1 ml of a trifluoroacetic anhydride/methylene chloride solution having a concentration of 2.4 mol/liter was added dropwise to the solution at an addition rate of 0.1 ml/min, followed by mixing.

After the completion of the dropwise addition and mixing, the resultant mixture solution was stirred at the above temperature for 10 minutes. To this mixed solution, 2 ml of a cyclohexanol/methylene chloride solution having a concentration of 1.0 mol/liter was added dropwise at an addition rate of 0.2 ml/min, followed by mixing.

After the completion of the dropwise addition and mixing, the resultant mixture solution was stirred at the above temperature for 10 minutes. To the resulting mixed solution, 4 ml of a triethylamine/methylene chloride solution having a concentration of 1.5 mol/liter was added dropwise at an addition rate of 0.4 ml/min, followed by mixing.

After the completion of the dropwise addition and mixing, the temperature of the resultant mixture solution was returned to room temperature and an internal standard agent was added thereto, and then the contents of the compounds in the mixed solution were measured by a gas chromatograph internal standard method. The measurement results are shown below.

| | |
|---|---|
| Cyclohexanone | 16% |
| Cyclohexyl trifluoroacetate | 60% |
| Cyclohexyl methylthiomethyl ether | 2% |
| Cyclohexanol | 14% |

Comparative Example 5 (Batch Synthesis Comparative Example)

In an argon gas atmosphere, 1 ml of a dimethyl sulfoxide/methylene chloride solution having a concentration of 4 mol/liter was charged in a Schrenk tube having an inner volume of 30 ml and then cooled to a temperature of −23° C. While stirring this solution using a magnetic stirrer, 1 ml of a trifluoroacetic anhydride/methylene chloride solution having a concentration of 2.4 mol/liter was added dropwise to the solution at an addition rate of 0.1 ml/min, followed by mixing.

After the completion of the dropwise addition and mixing, the resultant mixture solution was stirred at the above temperature for 10 minutes. To this mixed solution, 2 ml of a benzyl alcohol/methylene chloride solution having a concentration of 1.0 mol/liter was added dropwise at an addition rate of 0.2 ml/min, followed by mixing.

After the completion of the dropwise addition and mixing, the resultant mixture solution was stirred at the above temperature for 10 minutes. To the resulting mixed solution, 4 ml of a triethylamine/methylene chloride solution having a concentration of 1.5 mol/liter was added dropwise at an addition rate of 0.4 ml/min, followed by mixing.

After the completion of the dropwise addition and mixing, the temperature of the resultant mixture solution was returned to room temperature and an internal standard agent was added thereto, and then the contents of the compounds in the mixed solution were measured by a gas chromatograph internal standard method. The measurement results are shown below.

| | |
|---|---|
| Benzaldehyde | 39% |
| Benzyl trifluoroacetate | 40% |
| Benzyl alcohol | 20% |

Examples 31 to 39

Example of Synthesis of Decanal, 2-Octanone or Benzaldehyde from Decanol, 2-Octanol or Benzyl Alcohol by Using Single Mixer Manufactured by IMM GmbH Under the Conditions of a Reaction Temperature of −10 to 20° C. and a Reaction Time of 0.01 Seconds)

In each of Examples 31 to 39, SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.1 mm, length=3.2 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low-temperature water bath at a predetermined temperature described in Table 1. Furthermore, a SUS tube (inner diameter=1.0 mm, length=100 cm) was connected to the outlet of the apparatus through a PTFE connecting tube (inner diameter=1.0 mm, length=50 cm). Only this connecting tube was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed into one of two inlets of the second unit from the reaction solution outlet of the first unit and a reactant/methylene chloride solution having a concentration of 1.0 mol/L was fed through the other inlet of the second unit at a rate of 2.0 mL/min (step 2). The reaction product solution was rapidly fed into one of two inlets of the third unit through the reaction solution outlet of the second unit, and then a triethylamine/methylene chloride solution having a concentration of 1.4 mol/L was fed through the other inlet of the third unit at a rate of 4.0 mL/min (step 3). After feeding the solution for 4 minutes, the reaction solution produced in the third unit was sampled into sample bottle containing an internal standard substance through the outlet of the third unit. The yield of the product was determined by a GC internal standard method.

The Reactant (starting compound) fed into the second unit and the target reaction product obtained from the third unit are as follows.

Examples 31 to 33

Starting substance: Decanol
Target reaction product: Decanal

Examples 34 to 36

Starting substance: 2-octanol
Target reaction product: 2-octanone

Examples 37 to 39

Starting substance: Benzyl alcohol
Target reaction product: Benzaldehyde
The reaction results are shown in Table 1.

TABLE 1

| Example No. | Starting Substance | Reaction temperature (° C.) | Yield (%) Product | Yield (%) TFA ester | Yield (%) MTM ether | Non-reacted starting substance |
|---|---|---|---|---|---|---|
| 31 | Decanol | −10 | 66*[1] | 20*[4] | 7*[7] | 7 |
| 32 | Decanol | 0 | 66*[1] | 21*[4] | 6*[7] | 6 |
| 33 | Decanol | 20 | 68*[1] | 21* | 6*[7] | 4 |
| 34 | 2-octanol | −10 | 78*[2] | 3*[5] | 4*[8] | 10 |
| 35 | 2-octanol | 0 | 78*[2] | 3*[5] | 4*[8] | 9 |
| 36 | 2-octanol | 20 | 78*[2] | 2*[5] | 3*[8] | 12 |
| 37 | Benzyl alcohol | −10 | 79*[3] | 15*[6] | Uncalculated | 1 |
| 38 | Benzyl alcohol | 0 | 78*[3] | 14*[6] | Uncalculated | 0 |
| 39 | Benzyl alcohol | 20 | 75*[3] | 16*[6] | Uncalculated | 0 |

(Note)
*[1]Decanal
*[2]2-octanone
*[3]Benzaldehyde
*[4]Decyl trifluoroacetate
*[5]Octyl trifluoroacetate
*[6]Benzyl trifluoroacetate
*[7]Decyl methylthiomethyl ether
*[8]Octyl methylthiomethyl ether Examples 40 to 41

Example of Synthesis of Cyclohexanone from Cyclohexanol by Using Single Mixer Manufactured by IMM GmbH Under the Conditions of a Reaction Temperature of 10° C. and −10° C. and a Reaction Time of 0.01 Seconds In each of Examples 40 and 41, SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.1 mm, length=3.2 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low temperature water bath at a predetermined temperature described in Table 2. Furthermore, a SUS tube (inner diameter=1.0 mm, length=100 cm) was connected to the outlet of the apparatus using a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed into one of two inlets of the second unit from the reaction solution outlet of the first unit and a cyclohexanol/methylene chloride solution having a concentration of 1.0 mol/L was fed through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed through the other inlet of the third unit at a rate of 4.0 mL/min (step 3). After feeding the solution for 4 minutes, the reaction solution produced in the third unit was sampled into sample bottle containing an internal standard substance from the outlet of the third unit. The yield of the product was determined by a GC internal standard method. The reaction results are shown in Table 2.

TABLE 2

| Example No. | Starting Substance | Reaction temperature (° C.) | Yield (%) Product*[9] | Yield (%) TFA ester*[10] | Yield (%) MTM ether*[11] | Non-reacted Starting Substance |
|---|---|---|---|---|---|---|
| 40 | Cyclohexanol | −10 | 78 | 5 | 5 | 11 |
| 41 | Cyclohexanol | 10 | 80 | 4 | 4 | 9 |

(Note)
*[9]Cyclohexanone
*[10]Cyclohexyl trifluoroacetate
*[11]Cyclohexyl methylthiomethyl ether Example 42

Example of Synthesis of Cyclohexanone from Cyclohexanol by Using Single Mixer Manufactured by IMM GmbH Under the Conditions of a Reaction Temperature of 0° C. and a Reaction Time of 0.1 Seconds SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.25 mm, length=6.8 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low temperature water bath at 0° C. Furthermore, a SUS tube (inner diameter=1.0 mm, length=100 cm) was connected to the outlet of the apparatus through a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed from two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed into the second unit through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed into the third unit through the other inlet of the third unit at a rate of 4.0 mL/min (step 3). After feeding the solution for 4 minutes, the reaction solution produced in the third unit was sampled into sample bottle containing an internal standard substance through the outlet of the third unit. The yield of the product was determined by a GC internal standard method. The reaction results are shown in Table 3.

TABLE 3

| Example No. | Starting Substance | Reaction temperature (° C.) | Yield (%) | | | |
|---|---|---|---|---|---|---|
| | | | Product*$_9$ | TFA ester*$_{10}$ | MTM ether*$_{11}$ | Non-reacted Starting Substance |
| 42 | Cyclohexanol | 0 | 74 | 4 | 3 | 8 |

(Note)
*$_9$Cyclohexanone
*$_{10}$Cyclohexyl trifluoroacetate
*$_{11}$Cyclohexyl methylthiomethyl ether Examples 43 to 46

Example of Synthesis of Cyclohexanone from Cyclohexanol by Using Single Mixer Manufactured by IMM GmbH Under the Conditions of a Reaction Temperature of −20 to 10° C. and a Reaction Time of 0.5 Seconds In each of Examples 43 to 46, SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.5 mm, length=8.5 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low temperature water bath at a predetermined temperature described in Table 4. Furthermore, a SUS tube (inner diameter=1.0 mm, length=100 cm) was connected to the outlet of the apparatus through a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed into one of two inlets of the second unit through the reaction solution outlet of the first unit and a cyclohexanol/methylene chloride solution having a concentration of 1.0 mol/L was fed from the other inlet of the second unit at a rate of 2.0 mL/min (step 2). The reaction product solution was rapidly fed into one of two inlets of the third unit through the reaction solution outlet of the second unit, and then a triethylamine/methylene chloride solution having a concentration of 1.5 mol/L was fed through the other inlet of the third unit at a rate of 4.0 mL/min (step 3). After feeding the solution for 4 minutes, the reaction solution produced in the third unit was sampled into sample bottle containing an internal standard substance through the outlet of the third unit. The yield of the product was determined by a GC internal standard method. The reaction results are shown in Table 4.

TABLE 4

| Example No. | Starting Substance | Reaction temperature (° C.) | Yield (%) | | | |
|---|---|---|---|---|---|---|
| | | | Product*$_9$ | TFA ester*$_{10}$ | MTM ether*$_{11}$ | Non-reacted Starting Substance |
| 43 | Cyclohexanol | −20 | 77 | 5 | 5 | 11 |
| 44 | | −10 | 76 | 5 | 5 | 10 |
| 45 | | 0 | 77 | 3 | 3 | 8 |
| 46 | | 10 | 73 | 3 | 4 | 17 |

(Note)
*$_9$Cyclohexanone
*$_{10}$Cyclohexyl trifluoroacetate
*$_{11}$Cyclohexyl methylthiomethyl ether Example 47

Example of Synthesis of Cyclohexane from Cyclohexanol by Using Single Mixer Manufactured by IMM GmbH Under the Conditions of a Reaction Temperature of 0° C. and a Reaction Time of 1.2 Seconds SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=1 mm, length=5 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a low and constant-temperature water bath at 0° C. Furthermore, a SUS tube (inner diameter=1.0 mm, length=100 cm) was connected to the outlet of the apparatus through a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed through the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 5.

TABLE 5

| Example No. | Starting Substance | Reaction temperature (° C.) | Yield (%) | | | |
| | | | Product*9 | TFA ester*10 | MTM ether*11 | Non-reacted Starting Substance |
|---|---|---|---|---|---|---|
| 47 | Cyclohexanol | 0 | 69 | 2 | 2 | 17 |

(Note)
*9Cyclohexanone
*10Cyclohexyl trifluoroacetate
*11Cyclohexyl methylthiomethyl ether Example 48

Example of Synthesis of Cyclohexanone from Cyclohexanol by Using Single Mixer Manufactured by IMM GmbH Under the Conditions of a Reaction Temperature of 0° C. and a Reaction Time of 1.6 Seconds SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=1 mm, length=7 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low-temperature water bath at 0° C. Furthermore, a SUS tube (inner diameter=1.0 mm, length=100 cm) was connected to the outlet of the apparatus through a PTFE connecting tube (inner diameter=1.0 mm, length=50 cm). This connecting portion was dipped in a water bath at 30° C.

Using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed through the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 6.

TABLE 6

| Example No. | Starting Substance | Reaction temperature (° C.) | Yield (%) | | | |
| | | | Product*9 | TFA ester*10 | MTM ether*11 | Non-reacted Starting Substance |
|---|---|---|---|---|---|---|
| 48 | Cyclohexanol | 0 | 64 | 4 | 2 | 18 |

(Note)
*9Cyclohexanone
*10Cyclohexyl trifluoroacetate
*11Cyclohexyl methylthiomethyl ether Example 49

Example of Synthesis of Cyclohexanone from Cyclohexanol by Using Single Mixer Manufactured by IMM GmbH Under the Conditions of a Reaction Temperature of −10° C. and a Reaction Time of 2.4 Seconds SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=1 mm, length=10 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low temperature water bath at a predetermined temperature of −10° C. Furthermore, a SUS tube (inner diameter=1.0 mm, length=100 cm) was connected to the outlet of the apparatus through a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed through the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 7.

TABLE 7

| Example No. | Starting Substance | Reaction temperature (° C.) | Yield (%) | | | |
|---|---|---|---|---|---|---|
| | | | Product*$_9$ | TFA ester*$_{10}$ | MTM ether*$_{11}$ | Non-reacted Starting Substance |
| 49 | Cyclohexanol | −10 | 80 | 4 | 5 | 10 |

(Note)
*$_9$Cyclohexanone
*$_{10}$Cyclohexyl trifluoroacetate
*$_{11}$Cyclohexyl methylthiomethyl ether Examples 50 to 52

Example of Synthesis of Cyclohexanone from Cyclohexanol by Using Single Mixer Manufactured by IMM GmbH Under the Conditions of a Reaction Temperature of −20° C., 0° C. or 20° C. and a Reaction Time R1 of 0.01 Seconds and R2 of 0.02 Seconds In each of Examples 50 to 52, SUS tubes were connected to three Single Mixers Ver. 2 (Inlay: made of Ag plating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.1 mm, length=3.2 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=0.25 mm, length=3.2 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a constant low-temperature water bath at a predetermined temperature described in Table 8. Furthermore, a SUS tube (inner diameter=1.0 mm, length=100 cm) was connected to the outlet of the apparatus using a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.4 mol/L were respectively fed into the first unit through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed through the other inlet of the second unit at a rate of 2.0 mL/min (step 2). The reaction product solution of the first unit was rapidly fed from the reaction solution outlet of the second unit into one of two inlets of the third unit, and then a triethylamine/methylene chloride solution having a concentration of 1.4 mol/L was fed into the third unit through the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 8.

TABLE 8

| Example No. | Starting Substance | Reaction temperature (° C.) | Yield (%) | | | |
|---|---|---|---|---|---|---|
| | | | Product*$_9$ | TFA ester*$_{10}$ | MTM ether*$_{11}$ | Non-reacted Starting Substance |
| 50 | Cyclohexanol | −20 | 75 | 4 | 3 | 8 |
| 51 | | 0 | 76 | 3 | 3 | 8 |
| 52 | | 20 | 81 | 3 | 2 | 7 |

(Note)
*$_9$Cyclohexanone
*$_{10}$Cyclohexyltrifluoro acetate
*$_{11}$Cyclohexyl methylthiomethyl ether Examples 53 and 54

Example of Synthesis of Cyclohexanone from Cyclohexanol by Using Single Mixer Manufactured by IMM GmbH Under the Conditions of a Reaction Temperature of −20° C. or 0° C. and a Reaction Time of 0.01 Seconds In each of Examples 53 and 54, SUS tubes were connected to three Single Mixers Ver. 2 (Inlay: made of Agplating, fine liquid introducing channel width: 40 μm) manufactured by IMM GmbH (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.1 mm, length=3.2 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a low and constant-temperature water bath at a predetermined temperature described in Table 9. Furthermore, a SUS tube (inner diameter=1.0 mm, length=100 cm) was connected to the outlet of the apparatus using a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 2.0 mol/L and a trifluoroacetic anhydride/methylene chloride solution having a concentration of 2.0 mol/L were respectively fed into the first unit through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed into the other inlet of the second unit at a rate of 2.0 mL/min (step 2). The reaction product solution was rapidly fed from the reaction solution outlet of the second unit into one of two inlets of the third unit and, then, a triethylamine/methylene chloride solution having a concentration of 1.5 mol/L was fed into the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 9.

TABLE 9

| Example No. | Starting Substance | Reaction temperature (° C.) | Yield (%) | | | |
|---|---|---|---|---|---|---|
| | | | Product*$_9$ | TFA ester*$_{10}$ | MTM ether*$_{11}$ | Non-reacted Starting Substance |
| 53 | Cyclo- | −20 | 69 | 8 | 4 | 12 |
| 54 | hexanol | 0 | 66 | 8 | 4 | 13 |

(Note)
*$_9$Cyclohexanone
*$_{10}$Cyclohexyl trifluoroacetate
*$_{11}$Cyclohexyl methylthiomethyl ether Examples 55 and 56

Example of Synthesis of Cyclohexanone from Cyclohexanol by Using Single Mixer Manufactured by IMM GmbH Under the Conditions of a Reaction Temperature of −20° C. or 0° C. and a Reaction Time of 0.01 Seconds In each of Examples 55 and 56, SUS tubes were connected to three Single Mixers Ver. 2 (Inlay: made of Ag plating, fine liquid introducing channel width: 40 μm) manufactured by IMM Co. (Germany) to constitute a reaction apparatus. A SUS tube (inner diameter=1.0 mm, length=20 cm) was connected to each of two reaction reagent inlets of the first unit and then a reaction solution outlet of the first unit was connected to one of two reaction reagent inlets of the second unit through a SUS tube (inner diameter=0.1 mm, length=3.2 cm). A SUS tube (inner diameter=1.0 mm, length=20 cm) was connected to the other reaction reagent inlet of the second unit and then the reaction solution outlet of the second unit was connected to one of two reaction reagent inlets of the third unit through a SUS tube (inner diameter=1.0 mm, length=10 cm). A SUS tube (inner diameter=1.0 mm, length=20 cm) was connected to the other reaction reagent inlet of the third unit and then a SUS tube (inner diameter=1.0 mm, length=20 cm) was connected to a reaction solution outlet of the third unit. The upper portion of the present apparatus was dipped in a low-temperature water bath at a predetermined temperature shown in Table 10. Furthermore, a SUS tube (inner diameter=1.0 mm, length=100 cm) was connected to the outlet of the apparatus using a PTFE connecting tube (inner diameter=1.0 mm, length=50 cm). This connecting portion was dipped in a water bath at 30° C.

By using a gas-tight syringe manufactured by Hamilton Co., a dimethyl sulfoxide/methylene chloride solution having a concentration of 4.0 mol/L and a trifluoroacetic anhydride/methylene chloride solution having a concentration of 2.0 mol/L were respectively fed into the first unit through two inlets of the first unit at a rate of 1.0 mL/min (step 1), and then the reaction product solution of the first unit was rapidly fed from the reaction solution outlet of the first unit into one of two inlets of the second unit and a cyclohexanol/methylene chloride solution having a concentration of 1.0 mol/L was fed into the second unit through the other inlet of the second unit at a rate of 2.0 mL/min (step 2). The reaction product solution was rapidly fed from the reaction solution outlet of the second unit into one of two inlets of the third unit, and then a triethylamine/methylene chloride solution having a concentration of 1.5 mol/L was fed into the third unit through the other inlet of the third unit at a rate of 4.0 mL/min (step 3). After feeding the solution for 4 minutes, the reaction solution produced in the third unit was sampled from the outlet of the third unit into sample bottle containing an internal standard substance. The yield of the product was determined by a GC internal standard method. The reaction results are shown in Table 10.

TABLE 10

| Example No. | Starting Substance | Reaction temperature (°C.) | Yield (%) | | | |
|---|---|---|---|---|---|---|
| | | | Product*9 | TFA ester*10 | MTM ether*11 | Non-reacted Starting Substance |
| 55 | Cyclo-hexanol | −20 | 70 | 3 | 4 | 13 |
| 56 | | 0 | 73 | 3 | 4 | 15 |

(Note)
*9 Cyclohexanone
*10 Cyclohexyl trifluoroacetate
*11 Cyclohexyl methylthiomethyl ether

INDUSTRIAL APPLICABILITY

Our methods enables the production of a aldehyde or ketone compound from a corresponding primary alcohol or secondary alcohol at a comparatively high temperature, compared to the low temperature of −30° C. or lower in a conventional method, within a short time and with a high yield. Therefore it is practically useful.

The invention claimed is:

1. A method for producing an aldehyde or ketone compound by using a microreactor, comprising (1) mixing a liquid containing a sulfoxide compound with a liquid containing an activating agent for the sulfoxide compound to cause a reaction with each other and produce an activation reaction product of the sulfoxide compound; (2) mixing a liquid containing the activation reaction product of the sulfoxide compound with a liquid containing at least one member selected from primary and secondary alkyl alcohols to cause a reaction with each other and prepare a liquid containing an alkoxysulfonium salt; and (3) mixing the resulting liquid containing an alkoxysulfonium salt with a basic compound-containing liquid to cause a reaction with each other and prepare a liquid containing an aldehyde or ketone compound corresponding to the alkyl alcohol, wherein at least one of (1), (2) and (3) is carried out by using a microreactor.

2. The method according to claim 1, wherein the microreactor comprises two liquid-introducing channels having a fine cross-sectional profile for introducing two type of liquids; one micromixer portion for mixing and reacting two kinds of liquids introduced, with each other having a fine cross-sectional profile and connected to the liquid introducing channel; and one liquid discharging channel for discharging a reaction product liquid from the micromixer portion, having a fine cross-sectional profile.

3. The method according to claim 2, wherein two steps connected to each other are carried out by using a microreactor and a liquid discharging channel of a rector of an upstream step and a liquid introducing channel of a reactor of a downstream step connected to the upstream step, are connected with each other through a connecting capillary tube.

4. The method according to claim 1, wherein (1) and (2) are carried out in the microreactor.

5. The method according to claim 2, wherein the temperature of the liquids in the micromixer portion and the liquid discharging channel of the microreactor is adjusted to a desired value.

6. The method according to claim 3, wherein the temperature of the liquids in the connecting capillary tube is adjusted to a desired value.

7. The method according to claim 2, wherein the cross-sectional area of the liquid introducing channel, that of the liquid micromixer portion and that of the liquid discharging channel in the microreactor, are respectively, about 0.7 μm$^2$ to about 1 mm$^2$, about 0.7 μm$^2$ to about 1 mm$^2$ and about 0.7 μm$^2$ to about 1 mm$^2$.

8. The method according to claim 2, wherein a major diameter/minor diameter ratio of the cross section of the liquid introducing channel, the liquid micromixer portion and the liquid discharging channel in the microreactor, is 1 or more and the minor diameter is within a range from about 1 μm to about 1 mm.

9. The method according to claim 1, wherein, in the microreactor, the flow rate of the liquid to be discharged from the liquid micromixer is adjusted so that two kinds of liquids mixed with each other can be reacted to each other in the microreactor with a desired mixing efficiency and a desired retention time.

10. The method according to claim 1, wherein the residence time of the liquid in the microreactor is adjusted to within a range from about 0.001 to about 60 seconds.

11. The method according to claim 2, wherein (1) is carried out using a microreactor and the residence time of a mixed reaction solution of the sulfoxide compound-containing liquid with an activating agent-containing liquid in a portion of the microreactor between the inlet of the micromixer portion and the inlet of the reactor for (2) is in the range of from about 0.001 to about 60 seconds.

12. The method according to claim 1, wherein (1) is carried out in the microreactor and the reaction temperature in (1) is in the range of from about −80 to about +50° C.

13. The method according to claim 1, wherein (2) is carried out in the microreactor and the mixing reaction temperature in (2) is in the range of from about −80 to about +50° C.

14. The method according to claim 1, wherein the sulfoxide compound is selected from a dialkyl sulfoxide.

15. The method according to claim 1, wherein dimethyl sulfoxide is used as the dialkyl sulfoxide.

16. The method according to claim 1, wherein the activating agent for a sulfoxide compound is selected from the group consisting of acetic anhydride, oxalyl chloride, trifluoroacetic anhydride, trifluoromethanesulfonic anhydride, diphosphorus pentaoxide, chlorine, benzoyl chloride, acetyl chloride, methanesulfonyl chloride, p-toluenesulfonyl chloride, sulfur trioxide-pyridine complex and 2,4,6-trichloro-1,3,5-triazine.

17. The method according to claim 1, wherein the primary and secondary alcohols are selected from saturated and unsaturated C$_1$-C$_{20}$ aliphatic primary and secondary alcohols, or saturated and unsaturated aliphatic primary and secondary alcohols having an alicyclic aromatic hydrocarbon group, and saturated and unsaturated primary and secondary alcohols having a heterocyclic group.

18. The method according to claim 1, wherein the basic compound is selected from organic amine compounds.

19. The method according to claim 18, wherein the organic amine compound is selected from trialkylamines.

20. The method according to claim 1, wherein a molar ratio of the sulfoxide compound to be supplied in (1) to the primary or secondary alcohol to be supplied in (2) is within a range of from 1:1 to 20:1.

21. The method according to claim 1, wherein a molar ratio of the activating agent for a sulfoxide compound to be supplied in (1) to the primary or secondary alcohol to be supplied in (2) is within a range of from 1:1 to 2:1.

22. The method according to claim 1, wherein a molar amount of the base compound to be supplied in (3) is 2 to 20 times the molar amount of the primary or secondary alcohol to be supplied in (2).

23. The method according to claim 1, further comprising isolating the target aldehyde or ketone compound from the aldehyde or ketone compound-containing liquid prepared in (3).

* * * * *

UNITED STATES PATENT AND TRADEMARK OFFICE
CERTIFICATE OF CORRECTION

PATENT NO. : 7,332,632 B2 Page 1 of 1
APPLICATION NO. : 10/587369
DATED : February 19, 2008
INVENTOR(S) : Ataka et al.

It is certified that error appears in the above-identified patent and that said Letters Patent is hereby corrected as shown below:

In Column 62:

At line 41, please change "claim 1" to --claim 14--.

Signed and Sealed this

Sixteenth Day of December, 2008

JON W. DUDAS
*Director of the United States Patent and Trademark Office*